US006245055B1

United States Patent
Fulford et al.

(10) Patent No.: US 6,245,055 B1
(45) Date of Patent: Jun. 12, 2001

(54) LUER FITTING ADAPTER

(75) Inventors: Tony W. Fulford, Mt. Airy; David B. Adelman, Potomac, both of MD (US)

(73) Assignee: Roboz Surgical Instrument Co., Inc., Rockville, MD (US)

( * ) Notice: Subject to any disclaimer, the term of this patent is extended or adjusted under 35 U.S.C. 154(b) by 0 days.

(21) Appl. No.: 09/359,041

(22) Filed: Jul. 23, 1999

(51) Int. Cl.[7] .................................................. A61M 25/18
(52) U.S. Cl. ............................................ 604/533; 604/905
(58) Field of Search ................................. 604/240–243, 604/533, 534, 535, 905; 285/238

(56) References Cited

U.S. PATENT DOCUMENTS

| | | |
|---|---|---|
| 4,013,310 | 3/1977 | Dye . |
| 4,405,312 * | 9/1983 | Gross et al. ..................... 604/533 X |
| 4,473,369 * | 9/1984 | Lueders et al. .................. 604/533 X |
| 4,723,948 * | 2/1988 | Clark et al. ........................ 604/533 |
| 4,838,873 | 6/1989 | Landskron et al. . |
| 5,263,945 | 11/1993 | Byrnes et al. . |
| 5,776,117 | 7/1998 | Haselhorst et al. . |

* cited by examiner

Primary Examiner—Anhtuan T. Nguyen
(74) Attorney, Agent, or Firm—Leydig, Voit & Mayer, Ltd.

(57) ABSTRACT

An adapter for use in manufacturing medical appliances that can be inserted into a luer fitting. The adapter includes two right cylindrical halves that have been longitudinally grooved to engage a tubular delivery appliance, such as a needle. The two adapter halves can be produced with planar surfaces that are grooved after an order has been received, to accommodate a particular delivery appliance outside diameter. Each adapter half is then bonded to another adapter half using an adhesive, gripping the delivery appliance in a fluid-tight fit. Alternatively, the delivery appliance may be frictionally held by the adapter halves. The delivery appliance with the adapter can be easily connected to a luer fitting and such adapted appliances can be produced in small quantities economically.

9 Claims, 1 Drawing Sheet

LUER FITTING ADAPTER

TECHNICAL FIELD

The invention relates to an adapter for making a fluid-tight fit between a tube smaller than a luer fitting and a luer fitting. Specifically, the invention relates to an adapter that easily mounts to a tubular delivery appliance, such as a needle.

BACKGROUND

In medical practice a delivery appliance of one size must frequently be connected to a delivery source of a different size. One common example is a tubular needle designed to be used in a syringe. Disposable needles are well known in the medical sciences and are mass manufactured so that they can be easily inserted into a delivery source, utilized for their intended purpose, and then discarded. The luer connection hub or fitting was developed before disposable syringes and needles as a standard receptacle for receiving needles and other tubular delivery appliances.

The use of luer fitting appliances in standardized sizes requires manufacturers to supply delivery appliances that easily fit into a luer fitting. The most common method for manufacturing these delivery appliances is by insertion molding. In insertion molding, a delivery appliance is inserted into a mold and a luer fitting adapter is molded permanently around the delivery appliance. Since tubular delivery appliances are produced in a wide variety of diameters, a large number of different molding arrangements are needed to fill orders.

Insertion molding works well if the production quantities of the product are sufficiently high to justify the purchase or retrofitting of an insertion molding assembly machine to build the required luer-ready appliances. However, in may instances, manufacturers are not equipped to handle small volume orders for specific luer-ready appliances, and frequently delay production until the ordered quantity is large enough to justify the expense of retrofitting or purchasing the molding equipment or parts.

Accordingly, there is a need for a luer adapter for delivery appliances that can be manufactured inexpensively in small quantities so that small quantities of luer-ready delivery appliances can be supplied promptly.

SUMMARY OF THE INVENTION

The present invention provides for an adapter that can be produced and subsequently modified so that small quantities of various luer-ready delivery appliances can be manufactured economically.

In accordance with the invention, an adapter for adapting a tubular delivery appliance to a luer fitting comprises two right circular semi-cylinders. Each right circular semi-cylinder has a generally planar surface including a central longitudinal groove. When the two semi-cylinders are combined with their planar surfaces face-to-face, the adapter has an outer diameter for frictionally engaging the internal surface of a first tube and an inner channel for receiving a second tube. The first tube may be a luer fitting.

In accordance with the invention, there is also provided, for a luer fitting having an inside diameter and inside surface, a tubular delivery appliance having an outside diameter smaller than the inside diameter of a luer fitting, and an adapter for insertion into and engagement with the inside surface of the luer fitting in a fluid-tight fit, and holding the tubular delivery appliance in the luer fitting in a fluid-tight fit, the adapter comprising two right circular semi-cylinders, each right semi-cylinder including a generally planar surface having a central longitudinal groove, the semi-cylinders being bonded together with the planar surfaces face-to-face and the grooves aligned opposite each other so that the adapter has an outer diameter for frictionally engaging the luer fitting, the tubular delivery appliance being held in the grooves.

In accordance with the invention there is also provided, for a luer fitting having an inside diameter and inside surface, a tubular delivery appliance having an outside diameter smaller than an inside diameter of the luer fitting, and an adapter for insertion into and engagement with the inside surface of the luer fitting in a fluid-tight fit, holding the tubular delivery appliance in the luer fitting in a fluid-tight fit, the adapter comprising two right circular semi-cylinders, each right circular semi-cylinder including a generally planar surface having a central longitudinal groove, the two semi-cylinders being combined with the planar surfaces face-to-face and the grooves aligned opposite each other so that the adapter has an outer diameter for frictionally engaging the luer fitting and a central bore receiving and holding the tubular delivery appliance.

DETAILED DESCRIPTION

Figure 1:
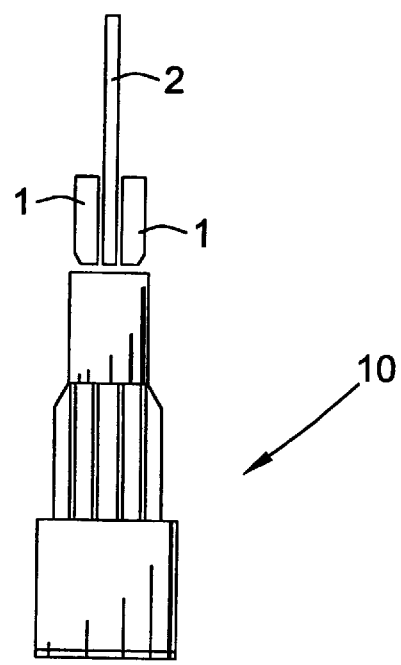
FIG. 1 is an exploded view showing an adapter according to an embodiment of the invention for connecting a tubular delivery appliance to a luer fitting.

As shown in the exploded view of FIG. 1, an adapter according to the invention includes two essentially identical adapter halves 1, sometimes referred to here as semi-cylinders, that are mounted on and grip a tubular delivery appliance, for example, a tubular needle 2. The needle 2 is only one example of a delivery appliance. Other examples include catheters, cannulae, and small tubes used for suction, drainage, feeding, and like applications. As used here, "delivery" means transport of a fluid, regardless of direction, and includes expulsion of a fluid from the needle 2 as well as extraction, such as of blood or by suction, from a source into the needle 2 or other delivery appliance.

Figure 2:
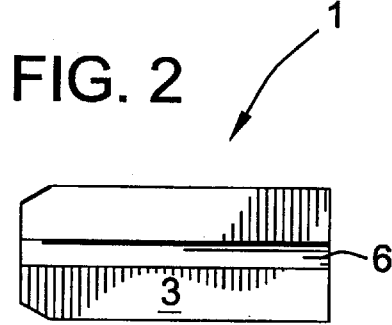
FIG. 2 is a plan view of an adapter half according to an embodiment of the invention.
Figure 3:
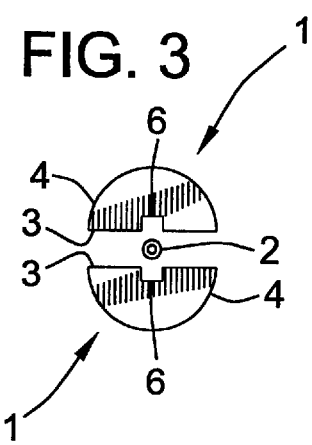
FIG. 3 is a cross sectional view of two adapter halves, before assembly of the adapter, and a tubular delivery appliance, all according to embodiments of the invention.

The needle 2 is held in a bore formed when the pair of adapter halves are brought into face-to-face contact. FIG. 2 shows one adapter half 1 in a plan view. In FIG. 3, two adapter halves are shown in cross section, ready to be joined, surrounding part of a tubular delivery appliance. Each adapter half 1 is a right circular semi-cylinder with a radius. Each semi-cylinder 1 has a generally planar surface 3, a curved outside surface 4 that is part of the surface of a cylinder, and end surfaces 5 transverse the planar surface and generally parallel to each other. Each of the planar surfaces 3 includes a central longitudinal groove 6.

When the adapter halves 1 are joined together with, their planar surfaces 3 face-to-face, and the grooves 6 aligned and opposite each other, the grooves form a bore in which the needle 2 is retained. The size and shape of the bore are discussed below. The outside diameter of the adapter, based on the radius of the outside curved surface 4, is dimensioned for a frictional, fluid-tight fit when inserted into a luer fitting 10 shown in FIG. 1. In other words, a fluid-tight fit is made to the inside surface of the fitting by the outside surfaces 4 of the adapter halves.

The adapter halves 1 may be acrylic and bonded to the tubular delivery appliance and to each other with an adhesive. Alternatively, the adapter halves may be metal and bonded face-to-face using an adhesive. Generally, if either the adapter halves or the appliance is made of a yielding material, such as acrylic, then the appliance must be bonded in the bore with an adhesive to establish a fluid-tight fit between the delivery appliance and the adapter halves 1.

As seen in the embodiment of FIGS. 2 and 3, the central longitudinal grooves 6 in the planar surface 3 of the adapter halves 1 have a generally rectangular cross section. Each groove 6 has two side walls 7 and a base wall 8 that extend the length of the adapter half. Preferably the depth of each side wall 7 is one half the width of the base wall 8. The base wall is dimensioned so that a delivery appliance fits snugly, bearing against the side and base walls as seen in FIG. 3.

The semi-cylinders 1 for the adapters according to the invention can be mass manufactured without grooving of the semi-cylinders. The grooving is delayed until assembly time, after the order quantity and the tubular delivery appliance outside diameter are known. After an order is placed, the semi-cylinders are grooved, a tubular delivery appliance is placed in a groove in one semi-cylinder, and the two adapter halves, i.e., semi-cylinders, are joined at the planar surfaces by an adhesive. In some cases the tubular delivery appliance must be mounted in the grooves with an adhesive but in other instances, the semi-cylinders may provide a sufficiently fluid-tight fit to the delivery appliance due to friction so that no adhesive is needed to hold the delivery appliance to the semi-cylinders. In fact, the friction may be sufficient to hold both semi-cylinders in place relative to the tubular delivery appliance.

The groove 6 need not be rectangular in cross-section. Any groove shape, such as a semi-circular cross-section, that permits placement of the tubular delivery appliance is usable. The rectangular cross-section provides a better frictional fit than a circular cross-section, but is more susceptible to leakage between an adapter half and a tubular delivery appliance so that use of an adhesive, filling any void space in the groove, particularly desirable.

Figure 4:
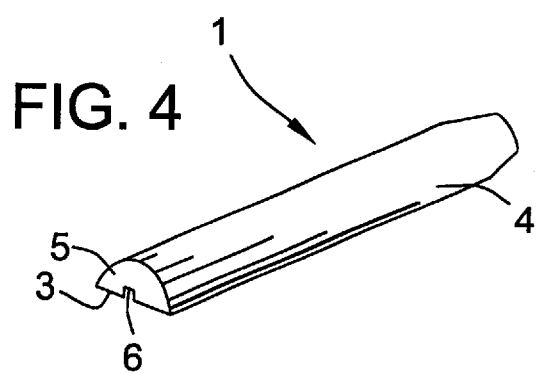
FIG. 4 is a prespective view of an adapter half according to an embodiment of the invention.

As shown in FIGS. 2 and 4, one end 9 of the adapter may have an oblique portion 11, i.e., be tapered. This tapered end of the device assists in inserting the adapter into a luer fitting and forming a fluid-tight seal to the fitting.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. An adapter for connecting a first tube of one diameter to a second tube of a different diameter comprising two separate right circular semi-cylinders not continuously connected to each other, each right circular semi-cylinder being a continuous solid body of material and having two ends, a length extending between the two ends, a generally planar surface including a central longitudinal groove extending between the two ends and having a uniform cross section with a substantially uniform depth perpendicular to the planar surface and a substantially uniform width parallel to the planar surface and extending between the two ends so that when the two semi-cylinders are combined with the planar surfaces face-to-face, the adapter has an outside diameter for frictionally engaging an inside surface of the first tube, and a central bore of uniform cross section throughout the length of the adapter for engaging an outside surface of the second tube.

2. The adapter of claim 1 wherein the two semi-cylinders are acrylic.

3. The adapter of claim 1 wherein at least one end of each of the semi-cylinders is tapered.

4. In combination, a tubular delivery appliance and an adapter for a luer fitting having an inside diameter and an inside surface, the tubular delivery appliance having an outside diameter smaller than the inside diameter of a luer fitting, the adapter for insertion into and engagement with the inside surface of the luer fitting in a fluid-tight fit, holding the tubular delivery appliance in a fluid-tight fit, the adapter comprising two separate right circular semi-cylinders not continuously connected to each other, each semi-cylinder being a continuous solid body of material and including two ends, a length extending between the two ends, a generally planar surface having a central longitudinal groove extending between the two ends and having a uniform cross section with a substantially uniform depth perpendicular to the planar surface and a substantially uniform width parallel to the planar surface and extending between the two ends, the semi-cylinders being bonded together with the planar surfaces face-to-face and the grooves aligned opposite each other, so that the adapter has an outer diameter for frictionally engaging the inside surface of the luer fitting and a central bore of uniform cross section through the length of the adapter receiving and holding the tubular delivery appliance.

5. The combination of claim 4 wherein the two semi-cylinders are acrylic.

6. The combination of claim 4, wherein the adapter is tapered on one end for inserting in the luer fitting.

7. In combination, a tubular delivery appliance and an adapter for a luer fitting having an inside diameter and an inside surface, the tubular delivery appliance having an outside diameter smaller than the inside diameter of a luer fitting, the adapter for insertion into and engagement with the inside surface of the luer fitting in a fluid-tight fit, holding the tubular delivery appliance in a fluid-tight fit, the adapter comprising two right circular semi-cylinders not continuously connected to each other, each semi-cylinder being a continuous solid body of material and including two ends, a length extending between the two ends, a generally planar surface having a central longitudinal groove extending between the two ends and having a uniform cross section with a substantially uniform depth perpendicular to the planar surface and a substantially uniform width parallel to the planar surface and extending between the two ends, the semi-cylinders being combined with the planar surfaces face-to-face and the grooves aligned opposite each other, so that the adapter has an outer diameter for frictionally engaging the inside surface of the luer fitting and a central bore of uniform cross section through the length of the adapter receiving and holding the tubular delivery appliance.

8. The combination of claim 6 wherein the adapter is tapered on one end for insertion in the luer fitting.

9. The combination of claim 7 wherein the two semi-cylinders are acrylic.

* * * * *